(12) United States Patent
Suedkamp et al.

(10) Patent No.: US 8,623,091 B2
(45) Date of Patent: Jan. 7, 2014

(54) DISTRACTIBLE INTERVERTEBRAL IMPLANT

(75) Inventors: Jann-Paul Suedkamp, Oberdorf (CH); Sean Saidha, Oberdorf (CH); Philipp Brun, Basel (CH)

(73) Assignee: DePuy Synthes Products, LLC, Raynham, MA (US)

( * ) Notice: Subject to any disclaimer, the term of this patent is extended or adjusted under 35 U.S.C. 154(b) by 158 days.

(21) Appl. No.: 13/170,557

(22) Filed: Jun. 28, 2011

(65) Prior Publication Data

US 2012/0071978 A1    Mar. 22, 2012

Related U.S. Application Data

(60) Provisional application No. 61/359,554, filed on Jun. 29, 2010.

(51) Int. Cl.
*A61F 2/44* (2006.01)

(52) U.S. Cl.
USPC ........................................ 623/17.16

(58) Field of Classification Search
CPC ..... A61F 2/4455; A61F 2/446; A61F 2/4465; A61F 2/447
USPC ........................................ 623/17.16
See application file for complete search history.

(56) References Cited

U.S. PATENT DOCUMENTS

| | | | |
|---|---|---|---|
| 5,697,977 A * | 12/1997 | Pisharodi | 606/279 |
| 5,865,848 A | 2/1999 | Baker | |
| 6,102,950 A | 8/2000 | Vaccaro | |
| 6,558,424 B2 | 5/2003 | Thalgott | |
| 6,562,074 B2 | 5/2003 | Gerbec et al. | |
| 6,648,917 B2 | 11/2003 | Gerbec et al. | |
| 6,852,129 B2 | 2/2005 | Gerbec et al. | |
| 6,863,673 B2 | 3/2005 | Gerbec et al. | |
| 7,618,458 B2 | 11/2009 | Biedermann et al. | |
| 8,128,700 B2 * | 3/2012 | Delurio et al. | 623/17.15 |
| 2004/0186570 A1 | 9/2004 | Rapp | |
| 2005/0125062 A1 * | 6/2005 | Biedermann et al. | 623/17.11 |
| 2005/0177235 A1 * | 8/2005 | Baynham et al. | 623/17.11 |
| 2007/0270968 A1 | 11/2007 | Baynham et al. | |
| 2007/0276375 A1 | 11/2007 | Rapp | |
| 2008/0033440 A1 | 2/2008 | Moskowitz et al. | |
| 2009/0005870 A1 * | 1/2009 | Hawkins et al. | 623/17.11 |

FOREIGN PATENT DOCUMENTS

| | | |
|---|---|---|
| EP | 1541096 A1 | 6/2005 |
| FR | 2874814 A1 | 3/2006 |
| WO | WO 2007/048012 A2 | 4/2007 |

\* cited by examiner

*Primary Examiner* — Ellen C Hammond
(74) *Attorney, Agent, or Firm* — Woodcock Washburn LLP

(57) ABSTRACT

A distractible intervertebral implant configured to be inserted in an insertion direction into an intervertebral space that is defined between a first vertebral body and a second vertebral body is disclosed. The implant may include a first body and a second body. The first body may define an outer surface that is configured to engage the first vertebral body, and an opposing inner surface that defines a rail. The second body may define an outer surface that is configured to engage the second vertebral body, and an inner surface that defines a recess configured to receive the rail of the first body. The second body moves in a vertical direction toward the second vertebral body as the second body is slid over the first body and the rail is received in the recess.

30 Claims, 9 Drawing Sheets

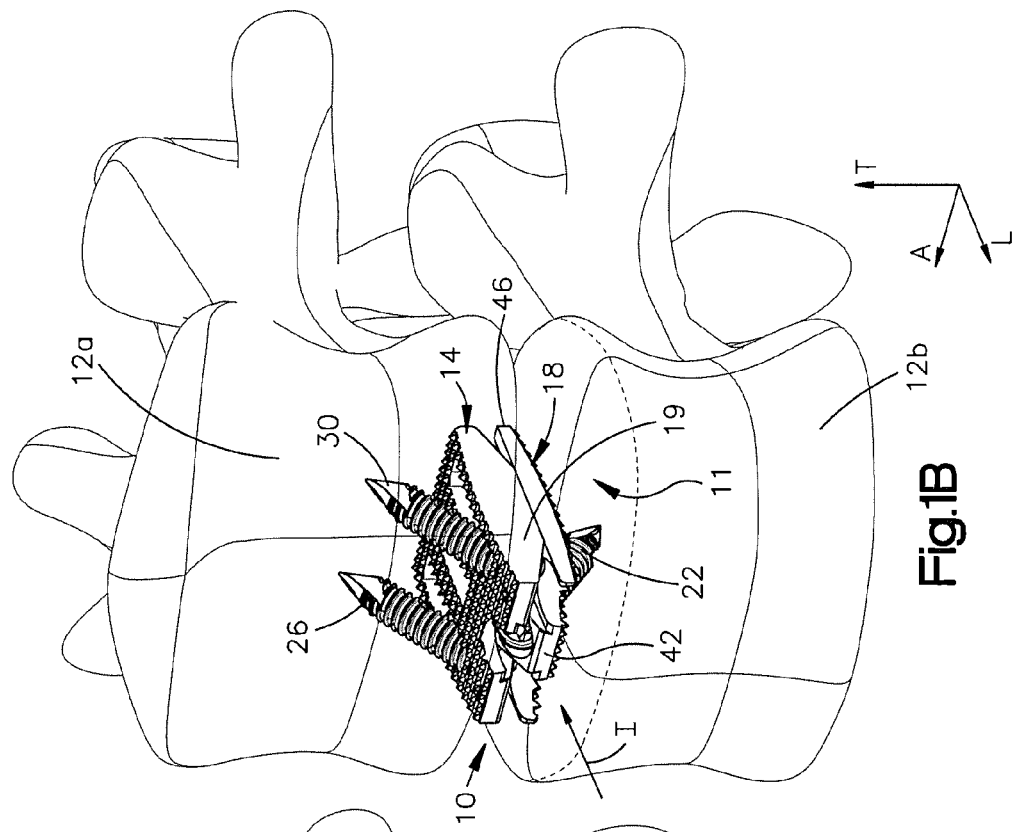
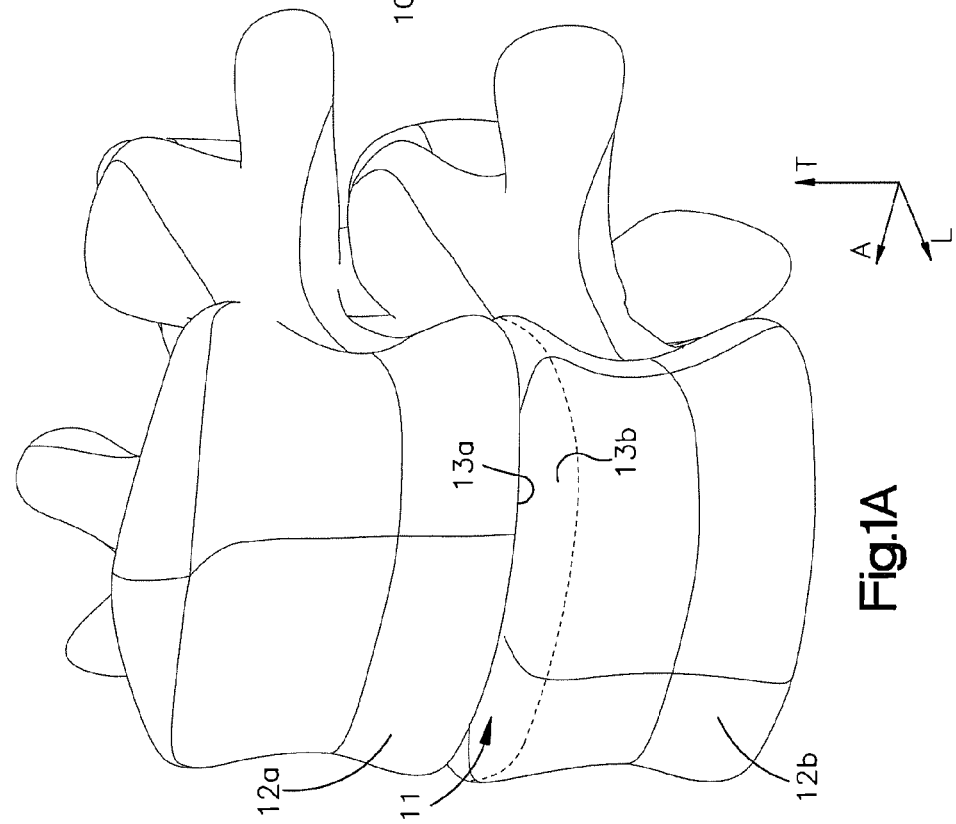

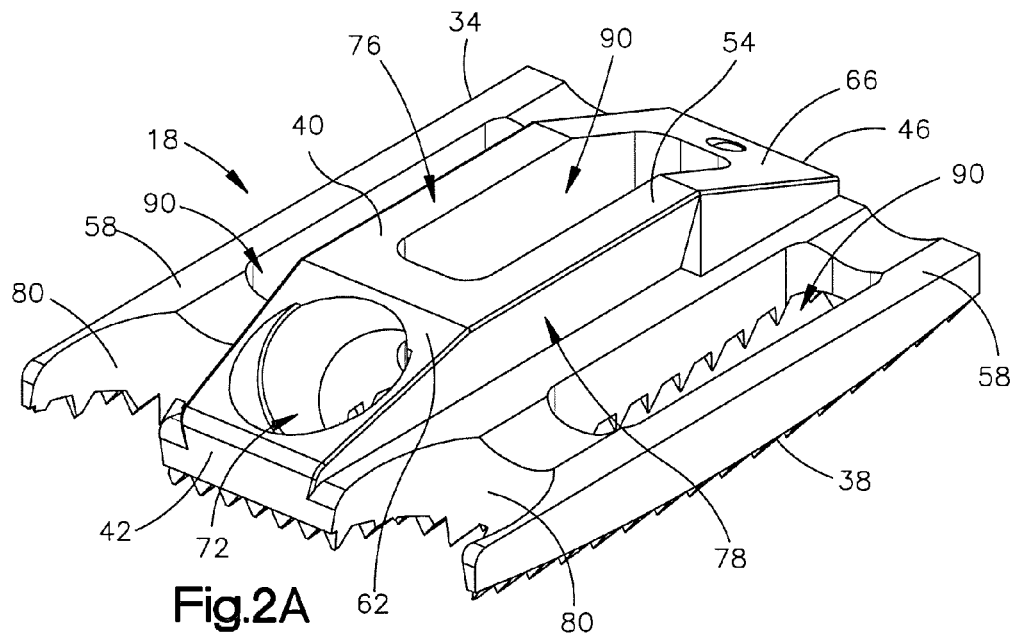
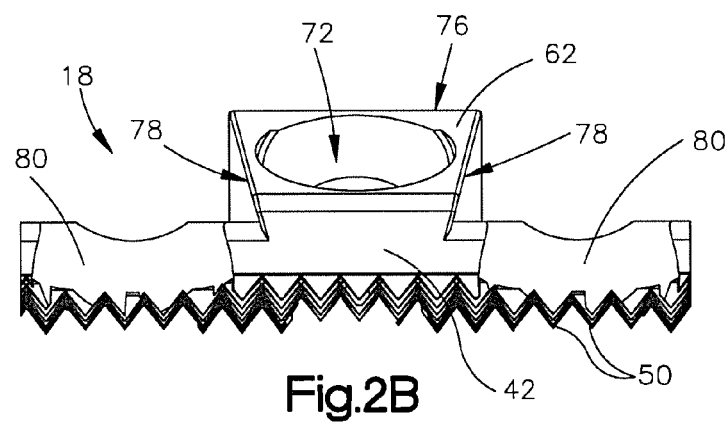
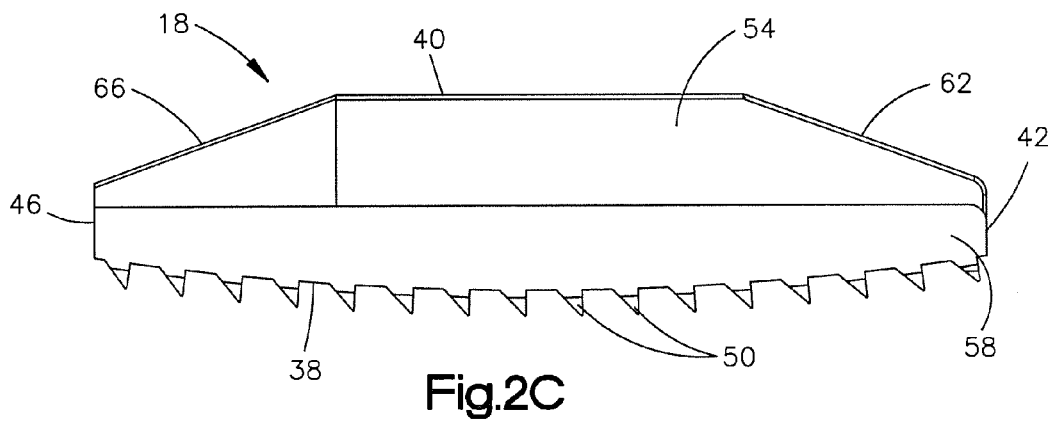

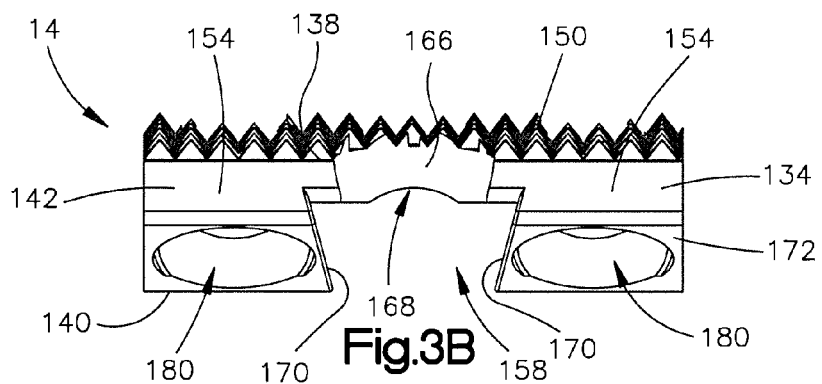
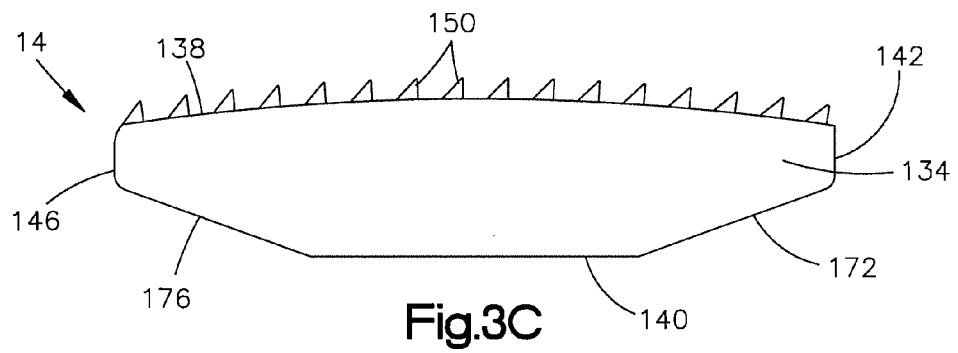
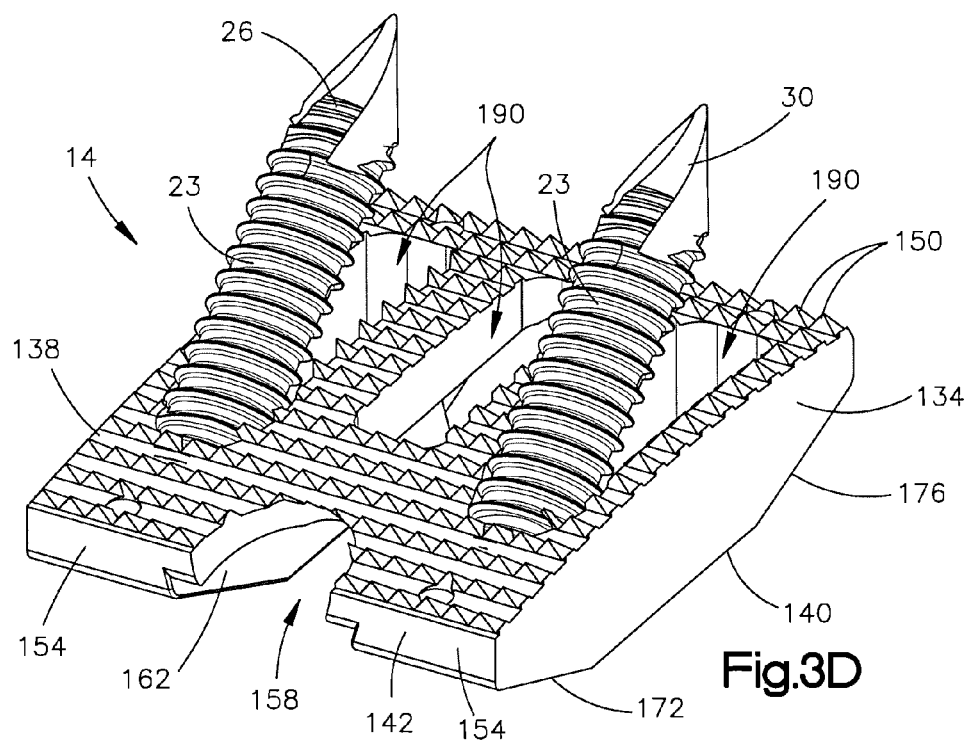

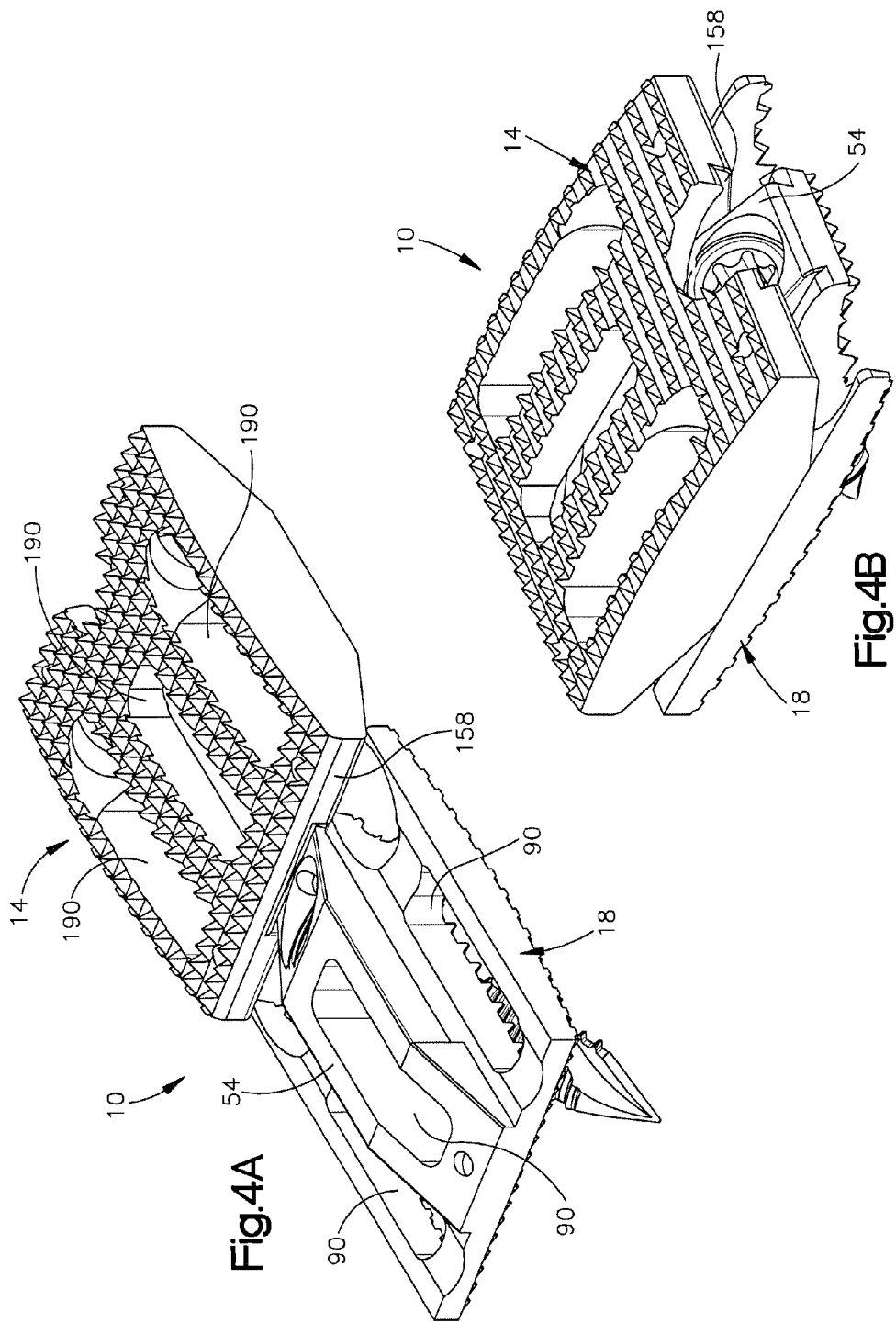

DISTRACTIBLE INTERVERTEBRAL IMPLANT

CROSS REFERENCE TO RELATED APPLICATIONS

This application claims the benefit of U.S. Provision Application Ser. No. 61/359,554 filed Jun. 29, 2010, the contents of which are incorporated herein by reference in their entirety.

BACKGROUND

Historically, after complete removal of a disc from between adjacent vertebrae, the adjacent vertebrae were fused together. This "spinal fusion" procedure, which is still in use today, is a widely accepted surgical treatment for symptomatic lumbar and cervical degenerative disc disease. More recently, disc arthoplasty may be utilized to insert an artificial intervertebral disc implant into the intervertebral space between adjacent vertebrae. Such a disc implant allows limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. Sagittal balance is defined as the equilibrium of the trunk with the legs and pelvis to maintain harmonious sagittal curves and thus the damping effect of the spine. In contrast with fusion techniques, total disc replacement preserves mobility in the motion segment and attempts to mimic physiologic conditions.

SUMMARY

A distractible intervertebral implant configured to be inserted in an insertion direction into an intervertebral space that is defined between a first vertebral body and a second vertebral body is disclosed. The implant may include a first implant body and a second implant body. The first implant body may define an outer surface that is configured to face the first vertebral body, and an opposing inner surface that defines a rail. The second implant body may define an outer surface that is configured to face the second vertebral body, and an inner surface that defines a recess configured to receive the rail of the first implant body. The second implant body is configured to move along the vertical direction as the second implant body is translated over the first implant body and the rail is received by the recess, so as to distract the first and second vertebral bodies.

In another embodiment, the implant may include a first implant body and a second implant body. The first implant body may include a pair of first side regions, and may define an outer surface that is configured to face the first vertebral body. The second implant body may also include a pair of second side regions. Each second side region may have an anterior end that angles toward the first implant body as the anterior end extends in a direction opposite the insertion direction. The second implant body may define an outer surface that is configured to face the second vertebral body. The anterior ends of the second implant body are configured to contact the first side regions of the first implant body as the second implant body is translated over the first implant body to thereby cause the outer surface of the second implant body to move away from the outer surface of the first implant body.

In another embodiment, a method for inserting an intervertebral implant into an intervertebral disc space defined between first and second vertebral bodies is disclosed. The method may include the step of inserting a first implant body into the intervertebral space such that as the first implant body is being inserted at least one of the first and second vertebral bodies moves away from the other vertebral body. The first implant body may include an outer surface that faces the first vertebral body, and an inner surface. The method may further include inserting a second implant body into the intervertebral space by sliding the second implant body over the inner surface of the first implant body. The second implant body may cause at least one of the first and second vertebral bodies to move away from the other as the second implant body is being inserted. The second implant body may include an outer surface that faces the second vertebral body.

BRIEF DESCRIPTION OF THE DRAWINGS

The foregoing summary, as well as the following detailed description of a preferred embodiment of the application, will be better understood when read in conjunction with the appended drawings. For the purposes of illustrating the distractable fusion implant and related instruments of the present application, there is shown in the drawings a preferred embodiment. It should be understood, however, that the application is not limited to the precise arrangements and instrumentalities shown. In the drawings:

FIG. 1A is a front perspective view of an intervertebral space defined between a superior vertebral body and an inferior vertebral body;

FIG. 1B is a front perspective view of a distractible intervertebral implant inserted into the intervertebral space, the implant including an inferior implant body and a superior implant body;

FIG. 2A is a front perspective view of the inferior implant body of the distractible fusion implant shown in FIG. 1B;

FIG. 2B is a front elevation view of the inferior implant body shown in FIG. 2A;

FIG. 2C is a side elevation view of the inferior implant body shown in FIG. 2A;

FIG. 3B is a front elevation view of the superior implant body shown in FIG. 3A;

FIG. 3C is a side elevation view of the superior implant body shown in FIG. 3A;

FIG. 3D is a front perspective view of the superior implant body shown in FIG. 3A with a pair of locking screws being inserted into a pair of bores of the superior implant body;

FIG. 4A is a back perspective view of the superior implant body being slid onto the inferior implant body;

FIG. 4B is a front perspective view of the superior implant body fully slid onto the inferior implant body to define the distractible fusion implant;

DETAILED DESCRIPTION

Figure 2D:
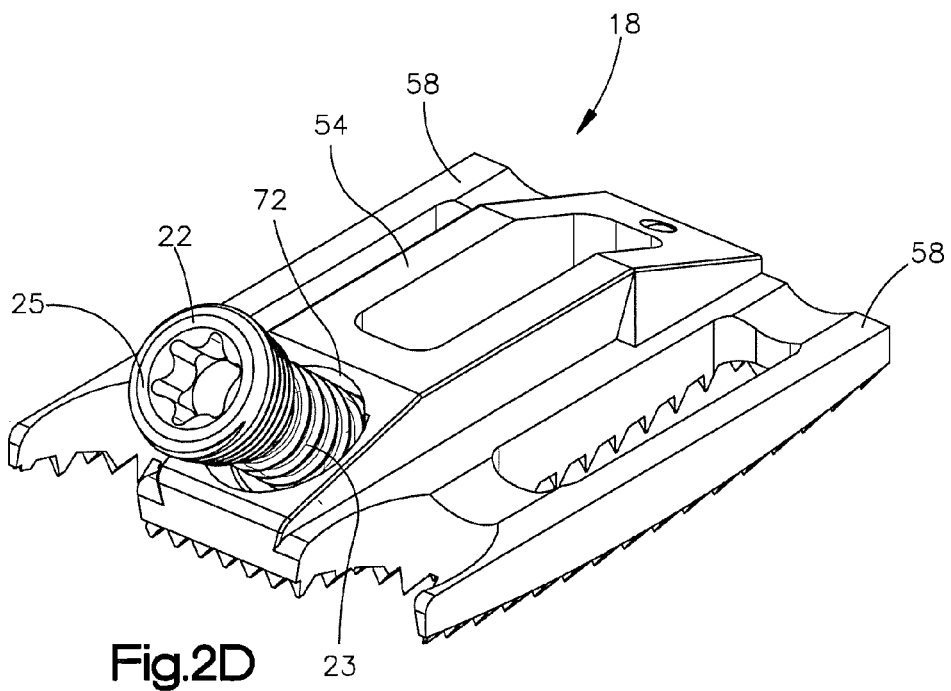
FIG. 2D is a front perspective view of the inferior implant body shown in FIG. 2A with a first fixation member being inserted into a bore of the inferior implant body.

Referring to FIG. 1A, an intervertebral space 11 is defined between a superior vertebral body 12a and an inferior vertebral body 12b. The superior vertebral body 12a generally defines an inferior endplate 13a or superior surface of the intervertebral space 11, and the adjacent inferior vertebral body 12b defines a superior endplate 13b or inferior surface of the intervertebral space 11. Thus, the intervertebral space 11 is disposed between the vertebral bodies 12a and 12b. The vertebral bodies 12a and 12b can be anatomically adjacent vertebral bodies, or can remain after a discectomy has been performed that removed a vertebral body from a location between the vertebral bodies. As illustrated, the intervertebral space 11 is illustrated after a discectomy, whereby the disc material has been removed or at least partially removed to prepare the intervertebral space 11 to receive a disc implant that can achieve height restoration. The intervertebral space 11 can be disposed anywhere along the spine as desired. Moreover, the superior vertebral body 12a may be considered a first or a second vertebral body and the inferior vertebral body 12b may be considered a first or a second vertebral body.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring also to FIG. 1B, an intervertebral implant, such as a distractable intervertebral implant 10, can be inserted into the intervertebral space 11 along a longitudinal insertion direction I, which can be a posterior direction in accordance with the illustrated embodiment or any other direction as desired. The distractable intervertebral implant 10 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the distractable intervertebral implant 10 is implanted into the intervertebral space 11 the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the distractable intervertebral implant 10 and its components as illustrated merely for the purposes of clarity and illustration.

Referring to FIG. 1B, the distractable intervertebral implant 10 includes a first or inferior implant body 18 and a second or superior implant body 14 that is coupled to the inferior implant body 18. The distractable intervertebral implant 10 can further include at least one first fixation member 22, illustrated as a first screw that couples the inferior implant body 18 to the inferior vertebral body 12b, and at least one second fixation member, such as second and third fixation members 26 and 30 illustrated as screws, that couple the superior implant body 14 to the superior vertebral body 12a. It should be understood that the fixation members 22, 26, and 30 may be also be configured as nails, blades, or graft. The distractable intervertebral implant 10 defines an anterior end 42 and an opposed posterior end 46. The anterior end 42 defines a trailing end of the distractable intervertebral implant 10 along the direction of insertion I, and the posterior end 46 defines a leading end of the distractable intervertebral implant 10 along the direction of insertion I.

The distractable intervertebral implant 10 may be partially or entirely formed from a metal, polymer, ceramic, allograft, or other artificial biomaterials such as beta-tricalcium phosphate. Suitable biocompatible materials or combinations of materials, may include PEEK, porous PEEK, carbon fiber-reinforced PEEK, titanium and titanium alloys, stainless steel, ceramic, polylactic acid, tantalum, magnesium, allograft, or other artificial biomaterials. The distractable intervertebral implant 10 presents an outer surface 19 that can be coated with any suitable material, such as hydroxyl apatite, beta-tricalcium phosphate, anodic plasma chemical treated titanium, or other similar coatings that improve osseointegration of the distractable intervertebral implant 10. As shown, the assembled implant 10 may be generally rectangular in shape, though it should be understood that all geometries are imaginable.

Referring to FIGS. 2A-2D the inferior implant body 18 includes a body portion 34 that defines a lower or inferior, or outer, engagement surface 38 configured to contact or otherwise face the superior endplate 13b of the inferior vertebral body 12b, an opposing inner surface 40, an anterior end 42, and an opposing posterior end 46. The body portion 34 further includes a plurality of engagement features 50, illustrated as teeth, that extend transversely out from engagement surface 38 and can be angled toward the anterior end 42 of the body portion 34. The engagement features 50 allow the inferior implant body 18 to easily translate along a posterior direction over the superior endplate of the inferior vertebral body during insertion of the inferior implant body 18 while at the same time provides immediate primary stability allowing the inferior implant body 18 to resist anterior migration. In other words, the engagement features 50 allow the inferior implant body 18 to easily slide in one direction, but if it were to slide in a second opposite direction, the teeth 50 would catch on the superior endplate 13b of the inferior vertebral body 12b to thereby prevent migration of the inferior implant body 18. It should be understood that the engagement features 50 can be shaped in any manner as desired, such as teeth, spikes, pyramids, cones, undefined geometries, rough surface topography, or independent bodies such a metal spikes that are embedded into the body portion 34 may be used.

As shown in FIGS. 2A-2D, the body portion 34, such as the inner surface 40, includes a middle region 54 and a first side region 58 extending from opposite sides of the middle region 54. The middle region 54 protrudes higher in the transverse vertical direction (or outwardly toward the superior implant body 14) with respect to the first side regions 58, and thus provides a longitudinally elongate rail that the superior implant body 14 can translate longitudinally along. In this way, the inner surface 40 of the body portion 34 defines the rail. In accordance with the illustrated embodiment, the anterior end 62 of the middle region 54 is angled upwards toward the superior implant body 14 as it extends toward the posterior end 46 of the body portion 34, and the posterior end 66 of the middle region 54 is angled upwards toward the superior implant body 14 as it extends toward the anterior end 42 of the body portion 34. As shown in FIG. 2A, the body portion 34 defines a bore 72 that extends through the anterior end 62. As shown in FIG. 2D, the bore 72 is configured to receive the first fixation member 22. The first fixation member 22 can include a shaft 23 and a head 25 that is dimensioned larger than the shaft 23. The bore 72 can likewise include a shaft-receiving region sized to receive the shaft 23, and a head receiving region sized to receive the head 25 when the fixation member 22 is fully received by the bore 72. The bore 72 can further be tapered and elongate along an angle toward the posterior end 46 of the body portion 34, such that the fixation member 22 is also elongate along the angle toward the posterior end 46 of the body portion 34 when received in the bore 72. The bore 72 can include a locking mechanism that engage a locking mechanism of the first fixation member 22, for instance a thread, a locking pin, a ratchet, a rough surface, etc. along one or both of the shaft 23 and the head 25. It should be understood that at least one or both of the shaft 23 and the head 25 can be substantially smooth and devoid of the locking mechanism. Likewise, at least one or both of the shaft-receiving region and the head-receiving region can be substantially smooth and devoid of the locking mechanism.

The middle region 54 further defines a top surface 76 and opposed side surfaces 78 that extend down from the top surface 76. The side surfaces 78 extend toward each other as they extend down from the top surface 76. That is, as the side surfaces 78 extend down from the top surface 76, the direction in which the side surfaces 78 extend includes a lateral component that extends toward the other side surface 78. Therefore, the side surfaces 78 and the top surface 76 define a dovetail shaped locking member. It should be understood, however, that the middle region may include configurations other than a dovetail shaped locking member. For example, the middle region may define an L-shaped locking member, a greater angulation longitudinal ratchet, etc.

As shown in FIG. 2A, the first side regions 58 include conical recesses 80 at their anterior ends. As shown, the conical recesses 80 are angled up as they extend toward the posterior end 46 of the body portion 34. As will be described later, the conical recesses 80 allow the second and third fixation members 26 and 30 to be inserted into the superior implant body 14 of the distractable intervertebral implant 10 at a specified angle.

The inferior implant body 18 can further include at least one graft window 90 such as a plurality of graft windows 90 that extend through at least one or more of the middle region 54 and the first side regions 58. Generally, each graft window 90 is elongate in the longitudinal direction, though it should be understood that any shape may be desired. The graft windows 90 are configured to receive autogenous bone graft or bone graft substitute such as Chronos, or DBM. For instance, the graft windows 90 may be pre-filled with the bone graft.

Referring to FIGS. 3A-3D, and 4A-4E the superior implant body 14 may be translated, for instance longitudinally, along the inferior implant body 18. As shown, the superior implant body 14 includes a body portion 134 that defines an upper or superior, or outer, engagement surface 138 configured to contact or otherwise face the inferior endplate 13a of the superior vertebral body 12a, an opposing interior surface 140, an anterior end 142, and an opposing posterior end 146. The body portion 134 further includes a plurality of engagement features 150 that extend transversely out from the engagement surface 138 and can be angled toward the anterior end 142 of the body portion 134. The engagement features 150 allow the superior implant body 14 to easily translate along a posterior direction under the inferior endplate of the superior vertebral body during insertion of the superior implant body 14 while at the same time provides immediate primary stability allowing the superior implant body 14 to resist anterior migration. In other words, the engagement features 150 allow the superior implant body 14 to easily slide in one direction, but if it were to slide in a second opposite direction, the engagement features 150 would catch on the inferior endplate 13a of the superior vertebral body 12a to thereby prevent migration of the superior implant body 14. It should be understood that the engagement features 150 can be shaped in any manner as desired, such as teeth, spikes, pyramids, cones, undefined geometries, rough surface topography, or independent bodies such a metal spikes that are embedded into the body portion 134 may be used.

As shown in FIGS. 3A-3D, the body portion 134, such as the inner surface 140, includes second side regions 154 that define a longitudinally elongate middle recess 158 configured to receive the longitudinally elongate rail of the body portion 34. The middle recess 158 extends into the body portion 134 from an inferior side of the superior implant body 14, and generally acts as a groove or channel that receives the middle region 54 of the inferior implant body 18. As shown, the middle recess 158 receives the middle region 54 of the inferior implant body 18 as the superior implant body 14 translates along the inferior implant body 18. An anterior end 162 of the middle recess 158 defines a conical recess 166 that is angled downwards. That is, the anterior end 162 of the middle recess 158 extends down as it extends toward the posterior end 146 of the body portion 134. Additionally, the anterior end 162 of the middle recess 158 defines a conical recess 166 that angles downward as it extends toward the posterior end 146 of the body portion 134. As will be described, the conical recess 166 enables the first fixation member 22 to be removed from the inferior implant body 18 of the distractable intervertebral implant 10 if so desired.

The middle recess 158 further defines a top surface 168 and opposing side surfaces 170 extending down from the top surface 168. The side surfaces 170 extend toward each other as they extend down from the top surface 168. That is, as the side surfaces 170 extend down from the top surface 168, the direction in which the side surfaces 170 extend includes a lateral component that extends toward the other side surface 170. Therefore, the side surfaces 170 and the top surface 168 define a dovetail shaped channel that receives the dovetail shaped middle region 54 of the inferior implant body 18. It should be understood, however, that the middle recess may include configurations other than a dovetail shaped channel. For example, the middle recess may define an L-shaped channel, a greater angulation longitudinal ratchet, etc.

Figure 3A:
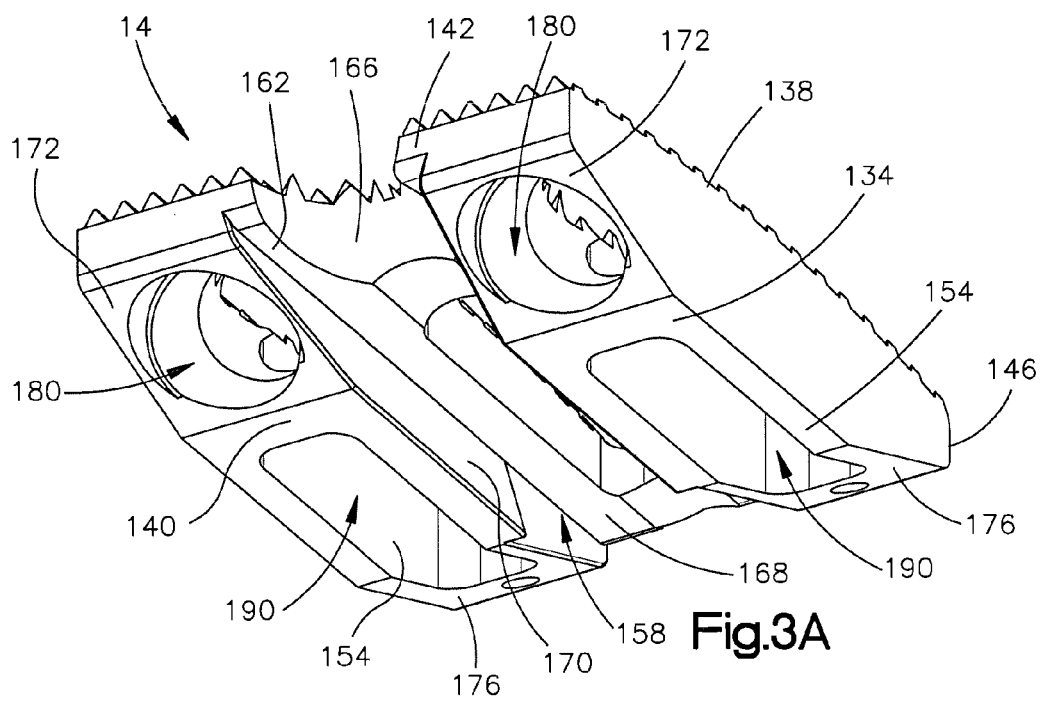
FIG. 3A is a bottom perspective view of the superior implant body of the distractible fusion implant shown in FIG. 1B.

The second side regions 154 each include an anterior end 172 and a posterior end 176 that are angled downwards. That is, the anterior end 172 of the second side regions 154 includes a surface that extend down or otherwise toward the inferior implant body 18 as they extend toward the posterior end 146 of the body portion 134, and the posterior end 176 of the second side regions 154 extend down or otherwise toward the inferior implant body 18 as they extend toward the anterior end 142 of the body portion 134. As shown in FIG. 3A, the body portion 134 defines a bore 180 that extends through each anterior end 172. As shown in FIG. 3D, each bore 180 is configured to receive one of the second and third fixation members 26 and 30. Like the first fixation member 22, the second and third fixation members can include a shaft 23 and a head 25 that is dimensioned larger than the shaft 23. The bores 180 can likewise include a shaft-receiving region sized to receive the shaft 23, and a head receiving region sized to receive the head 25 when the fixation members 26 and 30 are fully received by the bores 180. The bores 180 can further be tapered and elongate along an angle toward the posterior end 146 of the body portion 134, such that the fixation members 26 and 30 are also elongate along the angle toward the posterior end 146 of the body portion 134 when received in the bores 180. The bores 180 can include locking mechanisms that engage locking mechanisms of the second and third fixation members 26 and 30, for instance threads, locking pins, ratchets, rough surfaces, etc. along one or both of the shafts 23 and the heads 25. It should be understood that at least one or both of the shafts 23 and the heads 25 can be substantially smooth and devoid of the locking mechanisms. Likewise, at least one or both of the shaft-receiving regions and the head-receiving regions can be substantially smooth and devoid of the locking mechanisms.

As shown in FIGS. 3A and 3D, the superior implant body 14 can further include at least one graft window 190 such as a plurality of graft windows 190 that extend through at least one or more of the second side regions 154 as well as through the portion of the body portion 134 in which the recess 158 is defined. Generally, each graft window 190 is elongate in the longitudinal direction, though it should be understood that any shape may be desired. The graft windows 190 are configured to receive autogenous bone graft or bone graft substitute such as Chronos, or DBM. For instance, the graft windows 190 may be pre-filled with the bone graft.

As shown in FIG. 3D, the second and third fixation members 26 and 30 may be inserted into the bores 180 of the superior implant body 14 once the superior implant body 14 is fully slid onto the inferior implant body 18. The second and third fixation members 26 and 30 extend at an angle toward the posterior end of the distractable intervertebral implant 10. The second and third fixation members 26 and 30 engage the inferior endplate of the superior vertebral body to thereby securely attach the distractable intervertebral implant 10 to the superior vertebral body.

As shown in FIGS. 4A-4E, when the superior implant body 14 is fully slid onto the inferior implant body 18, the graft windows 190 of the superior implant body 14 align with the graft windows 90 of the inferior implant body 18. Therefore, the graft windows 90 and 190 define transverse channels that extend through the assembled implant 10. The graft windows 190 may be pre-filled with the bone graft.

As shown in FIGS. 4A-4D, the superior implant body 14 lockingly engages the inferior implant body 18 with respect to at least one or both of relative rotation and relative translation along a direction angularly offset with respect to the longitudinal insertion direction I when the recess 158 of the superior implant body 14 has received the rail of the inferior implant body 18. In that regard, the dovetail shaped recess 158 of the superior implant body 14 engages the dovetail shaped middle region 54 of the inferior implant body 18 when the inferior implant body 18 is received by the superior implant body 14 to create a form fit between the superior and inferior implant bodies 14 and 18. This form fit eliminates rotational degrees of freedom between the superior and inferior implant bodies 14 and 18. Other interlocking features between the superior implant body 14 and the inferior implant body 18 are envisioned to prevent translation in the longitudinal direction, such as a snap-action mechanism (e.g. PE-inlay or Prodisc-L). A third body (e.g. splint, pin, screw, bolt, glue) that is inserted after intraoperative assembly of the superior and inferior implant bodies 14 and 18 may also be used.

Figure 4C:
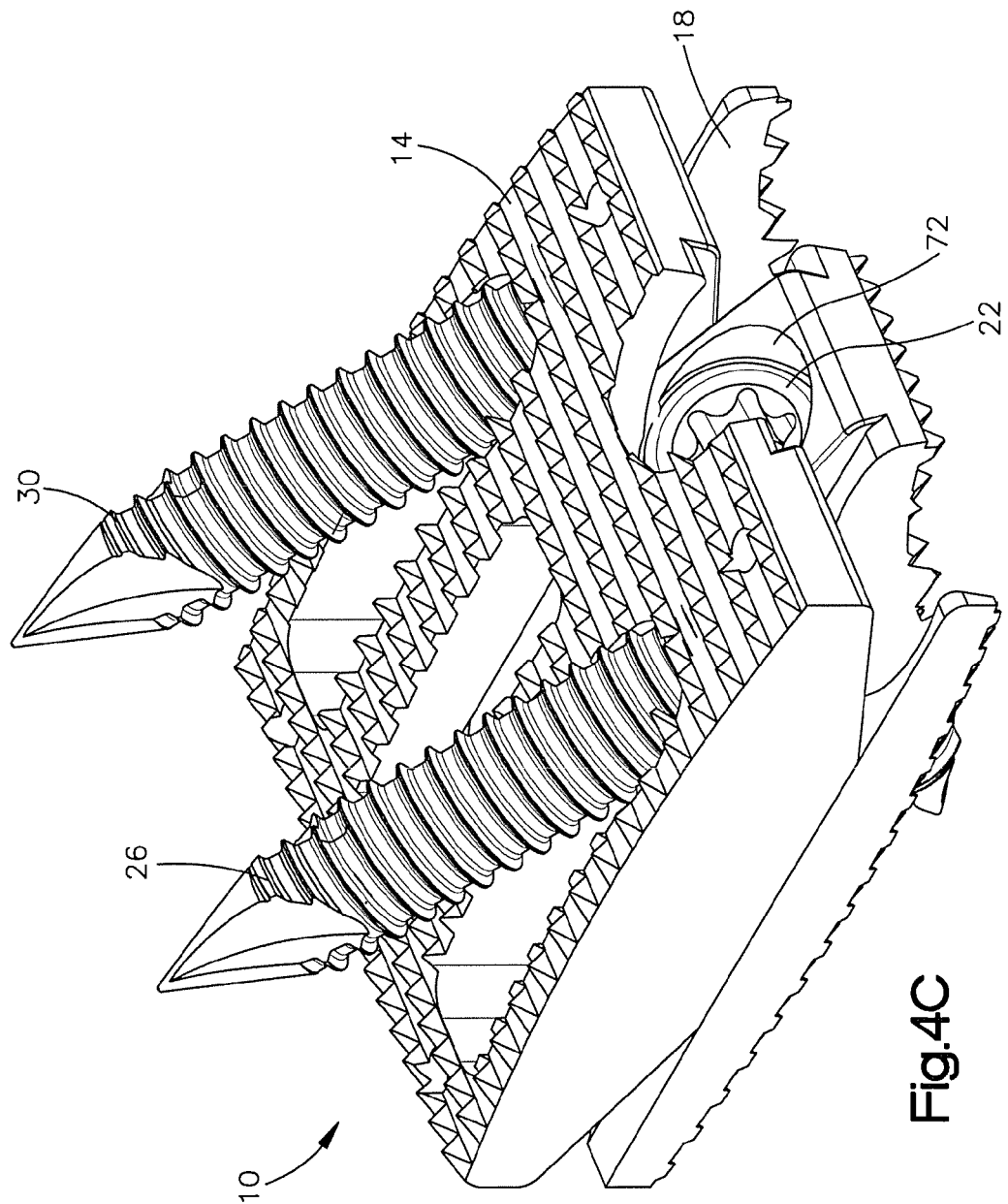
FIG. 4C is a front perspective view of the implant shown in FIG. 4B with three locking screws received within the bores of the superior and inferior implant bodies.
Figure 4D:
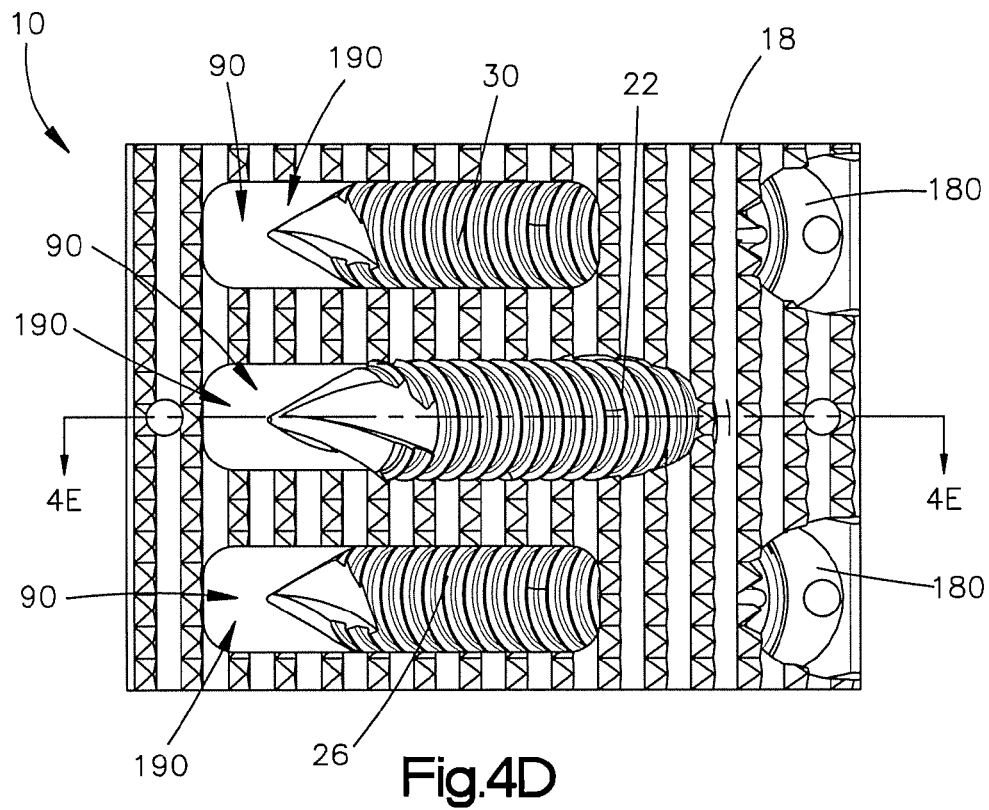
FIG. 4D is a top plan view of the implant shown in FIG. 4C.
Figure 4E:
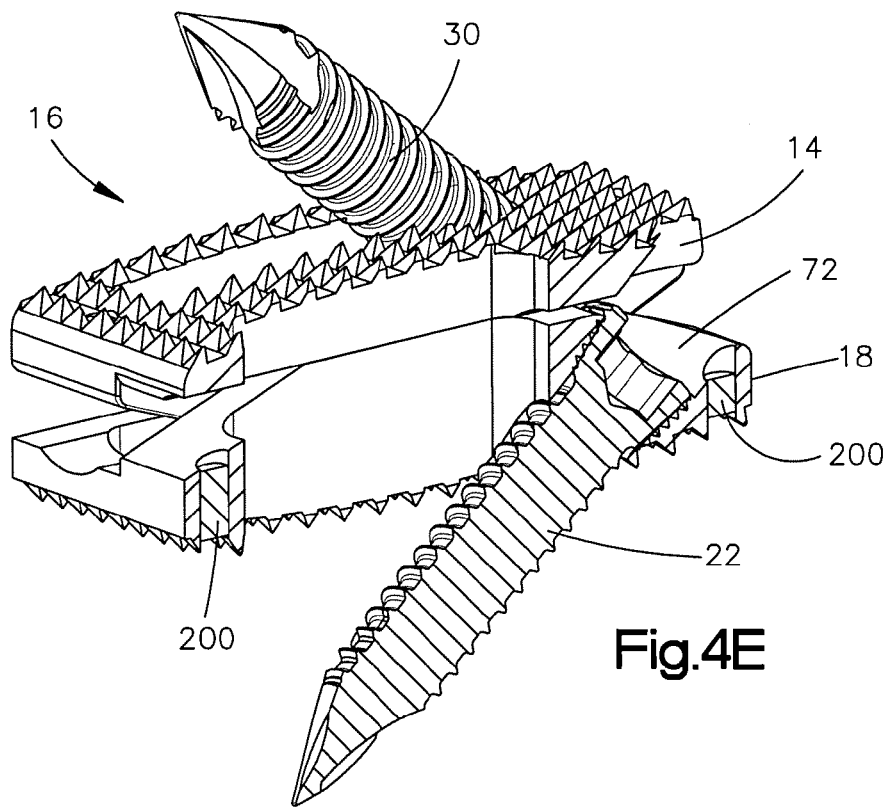
FIG. 4E is a cross-sectional view of the implant shown in FIG. 4D through the line 4E-4E.

As shown in FIGS. 4C-4E, the bores 72 and 180 are conical in shape. The conical shaped bores 72, 180 are configured to prevent the fixation members 22, 26, and 30 from being over inserted into the bores, and allow for angle stable fixation. The angle stable fixation prevents the fixation members not only from being over inserted but also from backing out. Thus, as each bore 72 and 180 receives its respective fixation members 22, 26, and 30 the heads of the fixation members 22, 26, and 30 will eventually abut the walls of the bores 72 and 180 to thereby prevent further insertion of the fixation members 22, 26, and 30. Such a configuration allows for a more stable fixation of the fixation members 22, 26, and 30. Furthermore, the angle stable connection between the fixation member's head and its counter part allow it to bear a bending moment.

As shown in FIG. 4E, the distractable intervertebral implant 10 may include marker pins 200, which may be used in case of a radiolucent base material that would not be visible in fluoroscopy/x-ray equipment. As shown, marker pins 200 may be buried within the body portion 34 of the inferior implant body 18. The marker pins 200 may be radioopaque to allow easy identification of the distractable intervertebral implant 10 in fluroscopique images. It should be understood that the implant 10 may include any number of pins 200, and that the pins 200 may also be buried within the superior implant body 14. Furthermore, instead of radiopaque marker pins 200, it may be possible to use polymers, ceramics, or biomaterials that include barium sulfate, or a similar substance. Barium sulfate (that is either homogeneously or inhomegeneously distributed in the base material) allows to make a radiopaque base material visible under fluoroscopy/x-ray equipment.

Figure 5B:
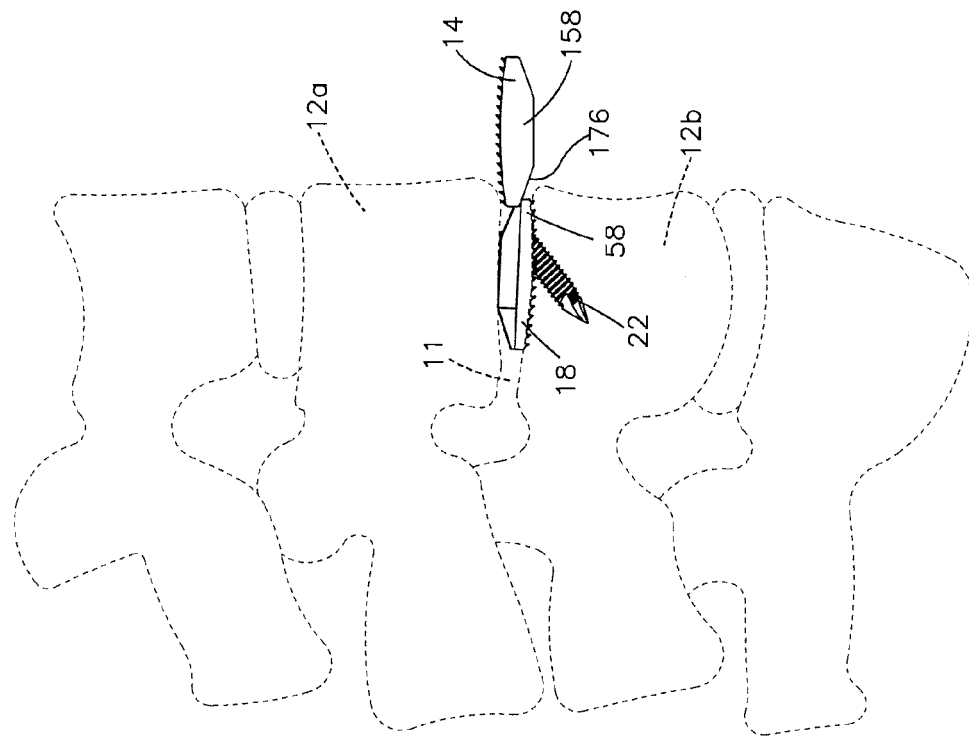
FIG. 5B is a side elevation view of the inferior implant body affixed to the inferior vertebral body with a first fixation member and a ramp portion of the superior implant body contacting an edge of the inferior implant body as it is being slid onto the intervertebral space.
Figure 5A:
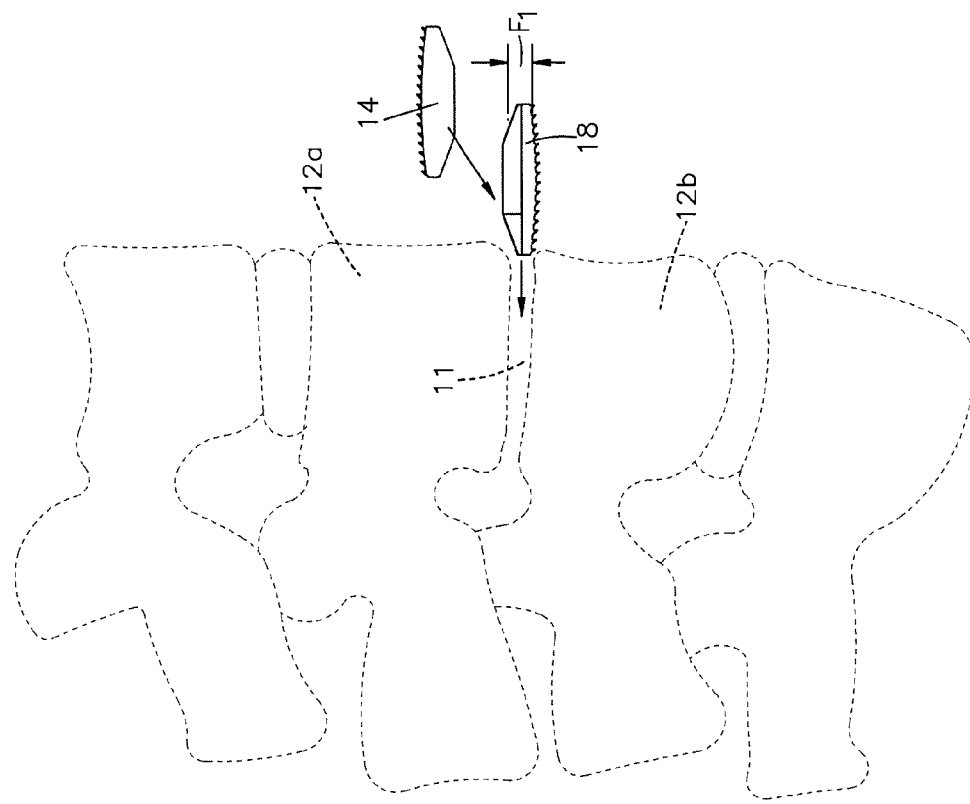
FIG. 5A is a side elevation view of the inferior implant body being slid into the intervertebral space defined between the superior and inferior vertebral bodies to thereby partially distract the vertebral bodies away from each other.
Figure 5D:
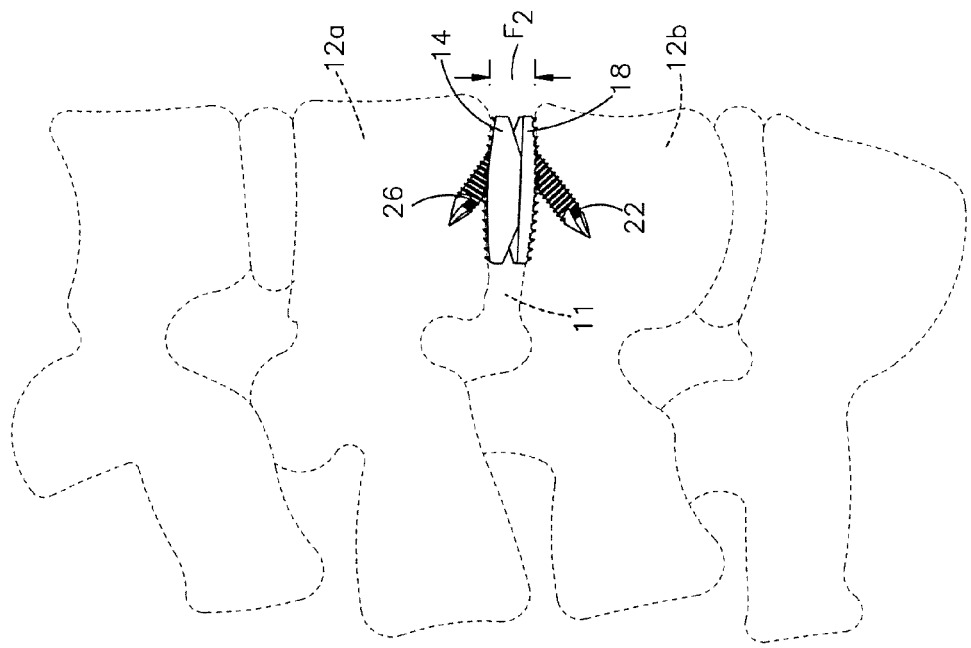
FIG. 5D is a side elevational view of the superior implant body affixed to the superior vertebral body with second and third locking screws.
Figure 5C:
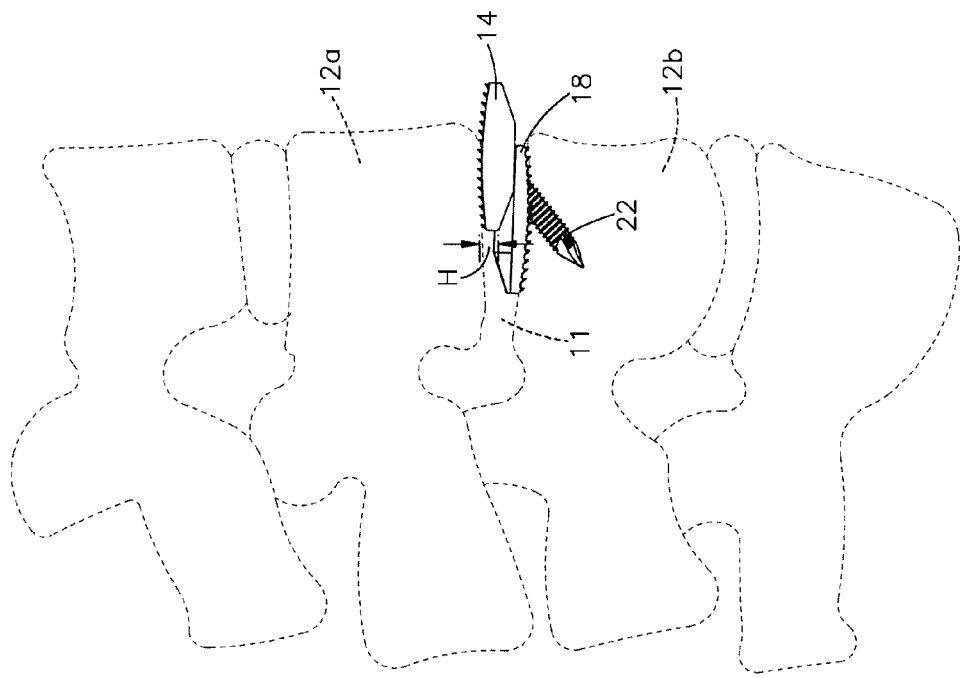
FIG. 5C is a side elevation view of the superior implant body further slid over the inferior implant body within the intervertebral space.

As shown in FIGS. 5A-5D, both the inferior implant body 18 and the superior implant body 14 may act as distractors as they are individually slid into the intervertebral space 11. As shown, in FIG. 5A, as the inferior implant body 18 is positioned within the intervertebral space 11 at least one of the superior vertebral body 12a and the inferior vertebral body 12b moves away from the other such that the superior and inferior vertebral bodies are separated by a first distance $F_1$. The first distance $F_1$ may be substantially equal to the transverse height of the inferior implant body 18. Once the inferior implant body 18 is properly positioned and attached to the inferior vertebral body 12b, the superior implant body 14 may be slid or otherwise translated over the inferior implant body 18 and into the intervertebral space 11. As shown in FIG. 5B, the angled posterior ends 176 of the superior implant body's second side regions 154 contact respective second side regions 58 of the inferior implant body 18. Because of the angled posterior ends 176 of the superior implant body 14, the superior implant body 14 will move toward the superior vertebral body 12a as the superior implant body 14 is slid over the inferior implant body 18, as shown in FIGS. 5B-5D to thereby cause at least one of the superior vertebral body 12a and the inferior vertebral body 12b to move away from the other such that the vertebral bodies are separated by a second distance $F_2$ that is greater than the first distance $F_1$. In this way, continuous distraction is achieved until the superior implant body 14 is fully assembled with the inferior implant body 18. As shown in FIG. 5D, the superior implant body 14 may move a distance H in an upward direction once it has been fully slid onto the inferior implant body 18. The distance H as well as the degree of distraction may depend on the angle at which the posterior ends 176 extend toward the anterior end of the superior implant body 14.

In operation, the inferior implant body 18 is first inserted into the intervertebral space. Once properly placed, the first fixation member 22 may be inserted into the bore 72 of the inferior implant body 18 and driven into the inferior vertebral body. Next the superior implant body 14 is pushed into the intervertebral space or otherwise slid over the inferior implant body 18. During insertion of the superior implant body 14, the superior implant body 14 slides over the inferior implant body 18. As described in relation to FIGS. 5A-5D, as the superior implant body 14 is sliding onto the inferior implant body 18, the superior implant body 14 moves up toward the superior vertebral body. Therefore, a continuous distraction of the inferior and superior vertebral bodies is achieved until the distractable intervertebral implant 10 is fully assembled. The superior implant body 14 interlocks with the inferior implant body 18 and builds a solid construct. The assembled implant 10 withstands translation and rotation in all six degrees of freedom.

Once the assembled implant 10 is properly positioned, the second and third fixation members 26 and 30 may be inserted into the bores 180 of the superior implant body 14. The second and third fixation members 26 and 30 engage the inferior endplate of the superior vertebral body to thereby securely attach the superior implant body 14 and therefore the distractable intervertebral implant 10 to the superior vertebral body.

Because the distractable intervertebral implant 10 may be placed into the intervertebral space 11 by first inserting the inferior implant body 18 and then the superior implant body 14, the distractable intervertebral implant 10 may be inserted into the intervertebral space 11 either from the anterior end of the patient or from the posterior end of the patient. In other words, by positioning the distractable intervertebral implant 10 in pieces rather than as a fully assembled construct the surgeon will be capable of accessing the intervertebral space 11 from the posterior end of the patient which is usually difficult, due to the limited amount of space. It should be understood that any surgical approach (i.e. anterior, anterolateral, lateral, extraforaminal, transforaminal, and posterior) may be considered.

It should be appreciated that the distractable intervertebral implant 10 described herein can be configured so as to provide a range of numerous possible geometries and angular relationships. For example, while the superior implant body 14 is described as having angled posterior ends that cause the superior implant body 14 to move upwards and thereby act as a distractor, it is possible to include an angled anterior end on the inferior implant body 18 to cause the superior implant body 14 to distract as it is inserted. Furthermore, it is envisioned that the superior implant body 14 could be inserted into the intervertebral space prior to the insertion of the inferior implant body 18.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

What is claimed:

1. A distractible intervertebral implant configured to be inserted into an intervertebral space along an insertion direction, the intervertebral space defined between a first vertebral body and a second vertebral body that is spaced from the first vertebral body along a vertical direction, the distractible intervertebral implant comprising:
    a first implant body that defines an outer surface configured to face the first vertebral body when the first implant body is disposed in the intervertebral space, and an opposed inner surface that defines an angled leading end; and
    a second implant body that defines an outer surface configured to face the second vertebral body when the second implant body is disposed in the intervertebral space, and an opposed inner surface that defines an angled leading end,
    wherein the inner surface of one of the first implant body and the second implant body defines a rail and the inner surface of the other of the first implant body and the second implant body defines a recess configured to receive the rail when either or both of the first and second implant bodies is translated relative to the other implant body along the insertion direction, and
    wherein the angled leading end of the first implant body is configured to cause the first vertebral body to move away from the second vertebral body along the vertical direction as the first implant body is inserted into the intervertebral space in the insertion direction and the angled leading end of the second implant body is configured to cause (i) the second implant body to move along the vertical direction as the second implant body is translated over the first implant body so as to further move the first vertebral body away from the second implant body along the vertical direction and (ii) the rail to be received by the recess such that the inner surfaces of the first and second implant bodies engage to provide stable mating between the first and second implant bodies.

2. The distractible intervertebral implant according to claim 1, wherein the first implant body includes a middle region and a pair of first side regions each first side region extending from an opposed side of the middle region, the middle region protruding higher in the vertical direction from the side regions to thereby define the rail.

3. The distractible intervertebral implant according to claim 2, wherein the middle region includes an anterior end and a posterior end, the posterior end angles toward the second implant body as the posterior end extends in a direction opposite the insertion direction, and the anterior end angles toward the second implant body as the anterior end extends in the insertion direction, one of the anterior end and the posterior end defining the leading angled end of the first implant body.

4. The distractible intervertebral implant according to claim 2, wherein the middle region defines a top surface and opposing side surfaces extending down from the top surface, each side surface extending toward the other as the side surfaces extend down form the top surface to thereby define a dovetail shaped locking member.

5. The distractible intervertebral implant according to claim 1, wherein the first implant body defines a bore that extends through the first implant body at an angle, the bore configured to receive a fixation member to thereby affix the first implant body to the first vertebral body.

6. The distractible intervertebral implant according to claim 1, wherein the second implant body includes a pair of second side regions, and the recess is defined between the second side regions of the pair of second side regions.

7. The distractible intervertebral implant according to claim 6, wherein the recess defines a top surface and opposing side surfaces that extend down from the top surface, each side surface extending toward the other as the side surfaces extend down from the top surface to thereby define a dovetail shaped channel.

8. The distractible intervertebral implant according to claim 6, wherein the second side regions each include an anterior end and a posterior end, the posterior ends angle toward the first implant body as the posterior ends extend in a direction opposite the insertion direction, and the anterior ends extend toward the first implant body as the anterior ends extend in the insertion direction, one of the anterior ends and the posterior ends defining the angled leading end of the second implant body.

9. The distractible intervertebral implant according to claim 8, wherein the anterior ends of each second side region defines a bore that extends completely through the second implant body at an angle, each bore configured to receive a fixation member to thereby affix the second implant body to the second vertebral body.

10. The distractible intervertebral implant according to claim 1, wherein each outer surface includes a plurality of engagement features.

11. The distractible intervertebral implant according to claim 1, wherein at least one of the first implant body and the second implant body includes a radiopaque marker.

12. The distractible intervertebral implant according to claim 1, wherein at least one of the first implant body and the second implant body includes a graft window that extends completely through the body in a direction that is transverse to the direction of insertion.

13. The distractible intervertebral implant according to claim 1, wherein the angled leading end of the first implant body is configured to cause the first and second vertebral bodies to distract as the first implant body is inserted into the intervertebral space along the insertion direction, such that when the first implant body is disposed in the intervertebral space the first and second vertebral bodies are spaced from each other along the vertical direction by a first distance, and the second implant body is configured to further distract the first and second vertebral bodies as the second implant body is inserted into the intervertebral space along the insertion direction such that the first and second vertebral bodies are spaced from each other by a second distance that is greater than the first distance when the second implant body is disposed in the intervertebral space.

14. The distractible intervertebral implant according to claim 1, wherein when the rail is received by the recess the inner surfaces of the first and second implant bodies engage to provide stable mating between the first and second implant bodies such that the second implant body is rotatably fixed relative to the first implant body.

15. The distractible intervertebral implant according to claim 1, wherein when the rail is received by the recess the inner surfaces of the first and second implant bodies engage to provide stable mating between the first and second implant bodies such that the second implant body is translatably fixed relative to the first implant body along a direction angularly offset with respect to the insertion direction.

16. The distractible intervertebral implant according to claim 1, wherein the inner surface of the first implant body defines the rail and the inner surface of the second implant body defines the recess.

17. The distractible intervertebral implant according to claim 1, wherein the inner surface of the second implant body further defines an angled trailing ends and a flat section that extends between the angled leading and trailing ends.

18. The distractible intervertebral implant according to claim 1, wherein the angled leading end of the second implant body causes the outer surface of the second implant body to move away from the outer surface of the first implant body.

19. The distractible intervertebral implant according to claim 1, wherein the first implant body and the second implant body are configured to interlock to form a solid construct when the rail is received by the recess.

20. A distractible intervertebral implant configured to be inserted into an intervertebral space along an insertion direction, the intervertebral space defined between a first vertebral body and a second vertebral body that is spaced from the first vertebral body along a vertical direction, the distractible intervertebral implant comprising:
  a first implant body that includes a pair of first side regions and defines an outer surface configured to face the first vertebral body when the distractible intervertebral implant is disposed in the intervertebral space; and
  a second implant body including a pair of second side regions and a middle region between the second side regions, each second side region having an anterior end that is angled toward the first implant body as the anterior end extends in the insertion direction, the second implant body defining an outer surface configured to face the second vertebral body when the distractible intervertebral implant is disposed in the intervertebral space,
  the first implant body further including an anterior end that is angled toward the second implant body as the anterior end extends in the insertion direction and a posterior end that is angled toward the second implant body as the posterior end extends in a direction opposite the insertion direction,
  wherein the middle region of the second implant body is configured to contact the anterior end of the first implant body as the second implant body is translated along the first implant body in the insertion direction and the anterior end of each second side region of the second implant body is configured to contact a respective one of the first side regions of the first implant body as the second implant body is translated along the first implant body in the insertion direction, thereby causing the outer surface of the second implant body to move away from the outer surface of the first implant body.

21. The distractible intervertebral implant according to claim 20, wherein the first implant body further includes a middle region between the pair of first side regions, the middle region of the first implant body protruding higher in the vertical direction from the first side regions to thereby define a rail.

22. The distractible intervertebral implant according to claim 21, wherein the middle region of the second implant body includes a recess defined between the pair of second side portions, the recess configured to receive the rail of the first implant body.

23. The distractible intervertebral implant according to claim 22, wherein the middle region of the first implant body includes an anterior end and a posterior end, the anterior end angles toward the second implant body as the anterior end extends in the insertion direction, and the posterior end angles toward the second implant body as the posterior end extends in a direction opposite the insertion direction.

24. The distractible intervertebral implant according to claim 22, wherein the middle region of the first implant body defines a top surface and opposing side surfaces extending down form the top surface, each side surface extending toward the other as the side surfaces extend down form the top surface to thereby define a dovetail shaped locking member.

25. The distractible intervertebral implant according to claim 24, wherein the recess defines a top surface and opposing side surfaces that extend down from the top surface, each side surface extending toward the other as the side surfaces extend down from the top surface to thereby define a dovetail shaped channel.

26. The distractible intervertebral implant according to claim 20, wherein the second implant body defines a pair of bores, each bore extending through the anterior end of a respective second side region of the second implant body, each bore configured to receive a fixation member to thereby affix the second implant body to the second vertebrae.

27. The distractible intervertebral implant according to claim 20, wherein the first implant body defines a bore that extends through the body at an angle, the bore configured to receive a fixation member to thereby affix the first body to the first vertebrae.

28. The distractible intervertebral implant according to claim 20, wherein each outer surface includes a plurality of engagement features.

29. The distractible intervertebral implant according to claim 20, wherein at least one of the first implant body and the second implant body includes a radiopaque marker.

30. The distractible intervertebral implant according to claim 20, wherein at least one of the first implant body and the second implant body includes a graft window that extends completely through the body in a direction that is transverse to the direction of insertion.

* * * * *